(12) United States Patent
Wang et al.

(10) Patent No.: US 11,072,740 B2
(45) Date of Patent: Jul. 27, 2021

(54) USE OF URANIUM-CONTAINING COMPOUND AS SCINTILLATOR

(71) Applicant: SOOCHOW UNIVERSITY, Suzhou (CN)

(72) Inventors: Shuao Wang, Suzhou (CN); Yaxing Wang, Suzhou (CN); Xuemiao Yin, Suzhou (CN)

(73) Assignee: SOOCHOW UNIVERSITY, Suzhou (CN)

(*) Notice: Subject to any disclaimer, the term of this patent is extended or adjusted under 35 U.S.C. 154(b) by 437 days.

(21) Appl. No.: 16/098,853

(22) PCT Filed: Apr. 8, 2018

(86) PCT No.: PCT/CN2018/082108
§ 371 (c)(1),
(2) Date: Nov. 3, 2018

(87) PCT Pub. No.: WO2019/184001
PCT Pub. Date: Oct. 3, 2019

(65) Prior Publication Data
US 2019/0300787 A1 Oct. 3, 2019

(30) Foreign Application Priority Data
Mar. 28, 2018 (CN) .......................... 201810264190.6

(51) Int. Cl.
*C09K 11/68* (2006.01)
*C01G 43/00* (2006.01)
(Continued)

(52) U.S. Cl.
CPC .......... *C09K 11/681* (2013.01); *C01B 35/128* (2013.01); *C01G 43/006* (2013.01);
(Continued)

(58) Field of Classification Search
CPC .... C01G 43/006; C01G 43/01; C01G 43/025; C01G 43/04; C01G 43/06; C01G 43/08; C01G 43/10; C01G 43/12; C09K 11/681
See application file for complete search history.

(56) References Cited

U.S. PATENT DOCUMENTS

2006/0027759 A1   2/2006   Jiang et al.

FOREIGN PATENT DOCUMENTS

| CN | 1250526 A | 4/2000 |
| CN | 106324655 A | 1/2017 |
| SU | 1304584 A1 | 11/1993 |

OTHER PUBLICATIONS

Schnaars. Structural and Vibrational Properties of U(VI)O2Cl42- and Pu(VI)O2Cl42-Complexes. Inorg. Chem. 2013, 52, 14138-14147 (Year: 2013).*

(Continued)

*Primary Examiner* — Matthew E. Hoban
(74) *Attorney, Agent, or Firm* — SZDC Law P.C.

(57) ABSTRACT

The invention discloses use of a uranium-containing compound as a scintillator. The uranium-containing compound is a uranium-containing organic-inorganic hybrid compound or a uranium-containing inorganic compound. The uranium-containing organic-inorganic hybrid compound is a uranium-containing organic carboxylate or a uranium-containing organophosphate. The uranium-containing inorganic compound is a uranium-containing non-metallate, a uranium-containing metal salt, or a uranium-containing halide. The invention discloses the uranium-containing organic-inorganic compound or the uranium-containing inorganic compound having intrinsic scintillating ability, and provides a new concept and method for the development of (organic-inorganic, inorganic) scintillators of various chemical compositions and configurations with the uranium element.

9 Claims, 5 Drawing Sheets (51) Int. Cl.
  *C01B 35/12*   (2006.01)
  *C09K 11/63*   (2006.01)
  *C07F 13/00*   (2006.01)
  *C07C 211/63*  (2006.01)
  *C09K 11/06*   (2006.01)

(52) U.S. Cl.
  CPC .......... *C07C 211/63* (2013.01); *C07F 13/005* (2013.01); *C09K 11/06* (2013.01); *C09K 11/63* (2013.01); *C09K 2211/1007* (2013.01); *C09K 2211/1014* (2013.01); *C09K 2211/188* (2013.01)

(56) References Cited

OTHER PUBLICATIONS

Li. An adaptive supramolecular organic framework for highly efficient separation of uranium via an in situ induced fit mechanism. J. Mater. Chem. A, 2015, 3, 23788 (Year: 2015).*

Lucks. Aqueous Uranium(VI) Complexes with Acetic and Succinic Acid: Speciation and Structure Revisited. Inorg. Chem. 2012, 51, 12288-12300 (Year: 2012).*

Wang, Yaxing et al., "Emergence of Uranium as a Distinct Metal Center for Building Intrinsic X-ray Scintillators," Angew. Chem. Int. Ed. vol. 57, Mar. 30, 2018, pp. 7883-7887.

* cited by examiner

USE OF URANIUM-CONTAINING COMPOUND AS SCINTILLATOR

This application is the national stage application of PCT/CN2018/082108, filed on Apr. 8, 2018, which claims priority to Chinese Patent Application No. 201810264190.6, filed on Mar. 28, 2018, which is incorporated by reference for all purposes as if fully set forth herein.

FIELD OF THE INVENTION

The present invention relates to the technical field of scintillators, and more particularly to use of a uranium-containing compound as a scintillator.

DESCRIPTION OF THE RELATED ART

Scintillating property upon irradiation refers to a process in which a material absorbs high-energy particles (α, β particles) or rays (X, or γ) and emits visible light. Materials with such a property are often referred to as "scintillator" because of their ability to visualize the "radiation" (ray-visible light-photoelectric conversion-imaging). Therefore, these materials are widely used in high-energy physics and nuclear physics experiments, space and astrophysics, medical imaging, environmental monitoring, safety inspection, nuclear non-proliferation detection, industrial non-destructive testing, petroleum logging, geological exploration and other fields.

Currently widely used scintillators are inorganic scintillators. Early inorganic scintillators include crystals such as ZnS, NaI, and CsI. Such pure inorganic salt crystals have low luminescence efficiency. Addition of a small amount of an activating agent such as $Tl^+$ ions to the inorganic salt crystals can further increase the luminescence efficiency. The scintillators of high fluorescence intensity developed at present include NaI:Tl, and CsI:Tl, etc. However, such ionic materials are more hygroscopic and require additional treatments in the actual production of the products. In addition, silicates of lanthanide elements doped mainly with luminescent $Ce^{3+}$ ions have high stability and large luminescence output, and thus are widely used. However, the single crystal growth technology of such materials is still less mature, for example, $Y_2Si_2O_7$:Ce cannot be melted uniformly, and the growth of large single crystals is still a problem. Another very important type of scintillator is bismuth germanate crystal ($Bi_4Ge_3O_{12}$, BGO), which has a density of about 7 g/cm$^3$, such that this type of crystal has high ray absorption ability, and can be widely used in, for example, high-energy physics, nuclear medical imaging and the like. However, the precursor $GeO_2$ is expensive, and it is important to find a cheap and high-performance scintillator in the development of scintillators.

In general, the radiation detection materials need to have (1) high luminescence output; (2) rapid response time; (3) good radiation and humidity stability; (4) good energy resolution and other performances; and (5) strong radiation resistance. Although various types of scintillators have been widely used, the use of each type of scintillator is limited to a specific requirement during practical application. Therefore, the development of scintillator materials is largely application-oriented. At present, the development of scintillator materials is mainly based on lattice matrices of heavy elements (silicates, aluminates, and borates, etc.) doped with luminescent elements such as $Ce^{3+}$, and $Eu^{2+}$ etc., to obtain better material properties. On the other hand, the development of scintillator materials also focuses on the growth of high-quality crystals such as $LaBr_3$:$Ce^{3+}$, $PbWO_4$, and $Bi_4Ge_3O_{12}$(BGO).

SUMMARY OF THE INVENTION

In order to solve the above technical problems, an object of the present invention is to provide use of a uranium-containing compound as a scintillator. The invention discloses a uranium-containing organic-inorganic compound or a uranium-containing inorganic compound having intrinsic scintillating ability, and as a ray scintillator, the compound improves the performance of the scintillator, and provides a new concept and method for the development of (organic-inorganic, inorganic) scintillators of various chemical compositions and configurations with the uranium element.

The present invention discloses use of a uranium-containing compound as a scintillator. The uranium-containing compound is a uranium-containing organic-inorganic hybrid compound or a uranium-containing inorganic compound. The uranium-containing organic-inorganic hybrid compound is a uranium-containing organic carboxylate of Formula (I) or a uranium-containing organophosphate of Formula (II):

The uranium-containing inorganic compound is a uranium-containing non-metallate of Formula (III), a uranium-containing metal salt of Formula (IV), or a uranium-containing halide of Formula (V):

(III)

In Formula (I), $R^1$ is selected from phenyl, substituted phenyl, or alkyl, and preferably the alkyl is $C^1$-$C^8$ alkyl; and n is 1 or 2.

In Formula (II), $R^2$ is selected from phenyl, substituted phenyl, or alkyl, and preferably the alkyl is $C^1$-$C^8$ alkyl; and n is 1 or 2.

In Formula (III), M is selected from the B, N, Si, Se, P, As, S or Te element; and n is 1 or 2.

In Formula (IV), Y is selected from the Mo, V, Cr, Nb, W, Re, Ga, Ge, Sb or Sn element; if m is 1, then n is 2; and if m is 2, then n is 1.

In Formula (V), X is selected from the F, Cl, Br or I element.

In Formulas (II), (III), and (IV), $A^{n+}$ is independently selected from tetramethylammonium cation, $Na^+$, $K^+$, $NH_4^+$, $Li^+$, $Rb^+$, $Cs^+$, $Mg^{2+}$, $Ca^{2+}$, $Sr^{2+}$, $Ba^{2+}$, $Pb^{2+}$ or $Bi^{2+}$.

In Formula (V), $B^+$ is selected from $Na^+$, $K^+$, $Li^+$, $Rb^+$, $Cs^+$ or wherein $R^3$, $R^4$, $R^5$ and $R^6$ are independently selected from hydrogen, alkyl, phenyl, or a nitrogen-containing phenyl.

Preferably, $R^1$ is phenyl or alkyl.

Preferably, in Formula (I), the uranium-containing organic carboxylate is $UO_2(C_9O_6H_4)(H_2O)$ (hereinafter referred to as SCU-9) having a structural formula of:

Traditional scintillators are mostly ion-bonded (such as CsI:Tl). The uranyl organic-inorganic hybrid material SCU-9 provided in the invention is covalently bonded and has high radiation resistance and water stability. SCU-9 has a density of 2.85 g/cm³ only, but has a radiation resistance that is significantly better than that of the existing commercial material CsI:Tl (with a density of 4.85 g/cm³) in the medical ray imaging applications (>20 KeV). Therefore, the radiation resistance of materials with uranyl as a luminescent center can be further enhanced by material design.

In a preferable embodiment, a method for preparing $UO_2(C_9O_6H_4)(H_2O)$ comprises the steps of:

dissolving uranyl nitrate ($UO_2(NO_3)_2 \cdot 6H_2O$), boric acid ($H_3BO_3$), and 1, 3, 5-benzenetricarboxylic acid in water, sealing, and performing reaction at 190-250° C., cooling and washing the resulting solution to obtain the $UO_2(C_9O_6H_4)(H_2O)$.

Preferably, the molar ratio of uranyl nitrate, boric acid, and 1, 3, 5-benzenetricarboxylic acid is 0.8-1:1-10:1-2.

Preferably, in Formula (II), n is 1, $R^2$ is phenyl, and $A^{n+}$ is tetramethylammonium cation.

Preferably, in Formula (II), the uranium-containing organophosphate has a structural formula of:

Preferably, in Formula (III), n is 1, M is the B element, and $A^{n+}$ is $Na^+$. In this case, the molecular formula is $Na[(UO_2)B_6O_{10}(OH)]$, which is referred to as NaBUO-4 hereinafter.

Preferably, in Formula (IV), n is 1, m is 2, Y is the Mo element, and $A^{n+}$ is $Na^+$, $Li^+$, $K^+$, $Rb^+$ or $Cs^+$;

or n is 2, m is 1, Y is the Mo element, and $A^{n+}$ is $Mg^{2+}$, $Ca^{2+}$, $Sr^{2+}$, $Ba^{2+}$, $Pb^{2+}$ or $Bi^{2+}$.

Figure 1:
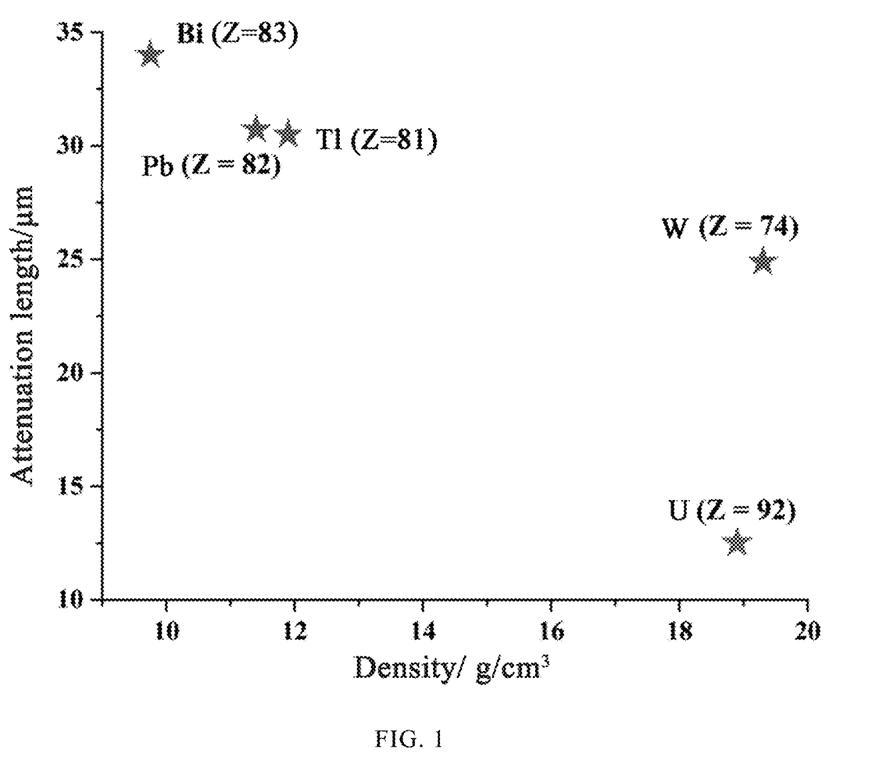
FIG. 1 is a chart showing the radiation resistance vs element density.

Preferably, in Formula (V), X is the Cl element, and B⁺ is wherein, $R^3$, $R^4$, $R^5$ and $R^6$ are independently selected from hydrogen, alkyl, phenyl, or a nitrogen-containing phenyl. Preferably, $B^+$ is $NH_4^+$ or The invention proposes new use of a uranium-containing compound as a scintillator. Uranium has excellent luminescent property and material designability, and is a luminescent element that has not yet been introduced into the scintillator research and development. The most stable state of the element uranium is hexavalent, and is in the chemical form of uranyl ($UO_2^{2+}$). An important feature is the emission of green fluorescence caused by the molecular orbital transition of uranyl. Compared with the lanthanide luminescent elements, the luminescence of uranyl is intrinsic, and energy can be directly transmitted from an excitation source to the element itself for emitting light without the introduction of an energy-transferring ligand. Moreover, uranium is the last stable element that exists on the earth, and has high density and radiation resistance. As shown in FIG. 1, uranium has the highest radiation resistance compared with the core elements W, Pb, Bi, Tl, and so on in popular scintillators.

By means of the above technical solutions, the invention has the following advantages.

The present invention provides a method and a concept of using the element uranium as a scintillator, including a uranium-containing organic-inorganic hybrid compound or a uranium-containing inorganic compound. The material has superior performances and large design space, thereby providing a brand-new design concept and method for scintillator materials.

DETAILED DESCRIPTION OF THE PREFERRED EMBODIMENTS

The invention will be further illustrated in more detail with reference to the accompanying drawings and embodiments. It is noted that, the following embodiments only are intended for purposes of illustration, but are not intended to limit the scope of the present invention.

Embodiment 1

Synthesis of SCU-9 Crystal

The reactants $UO_2(NO_3)_2 \cdot 6H_2O$, $H_3BO_3$, and 1,3,5-benzenetricarboxylic acid were placed into a polytetrafluoroethylene reactor at a molar ratio of 1:10:1, a small amount of deionized water was added to dissolve the reactants. The resulting mixture was sealed, heated up to 200° C. and heated for 3 days, and then gradually cooled to room temperature. The product was washed with a large amount of boiling water, until the boric acid was completely dissolved. The resulting crystalline product was washed with ethanol, and then air dried at room temperature, to obtain the SCU-9 crystal. A central metal $UO_2^{2+}$ of the crystalline product is coordinated with a carboxylic acid to form a one-dimensional linear polymer with a density of 2.85 g/cm³.

Figure 2:
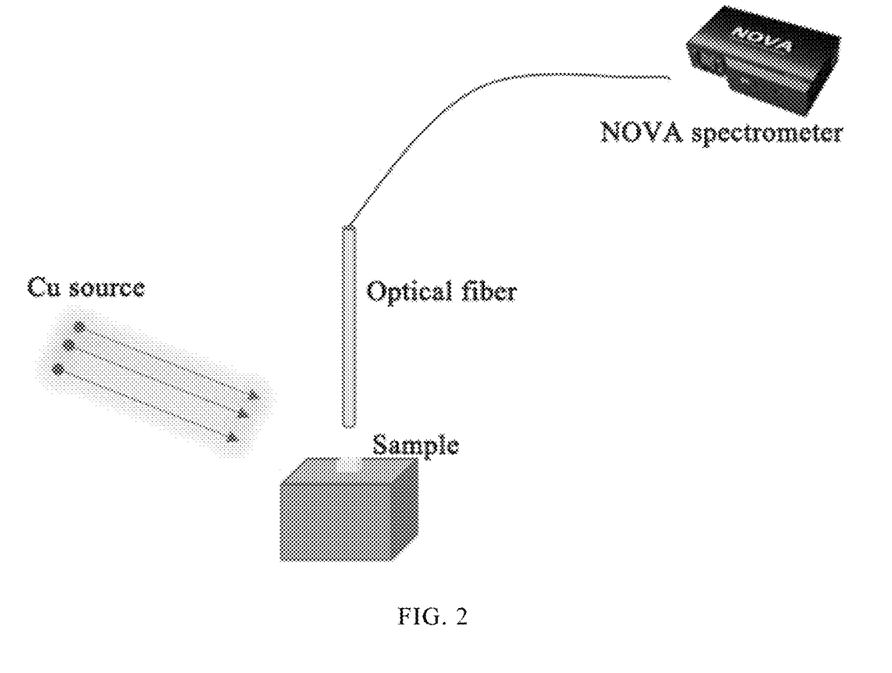
FIG. 2 is a schematic view of an X-ray tester.
Figure 3:
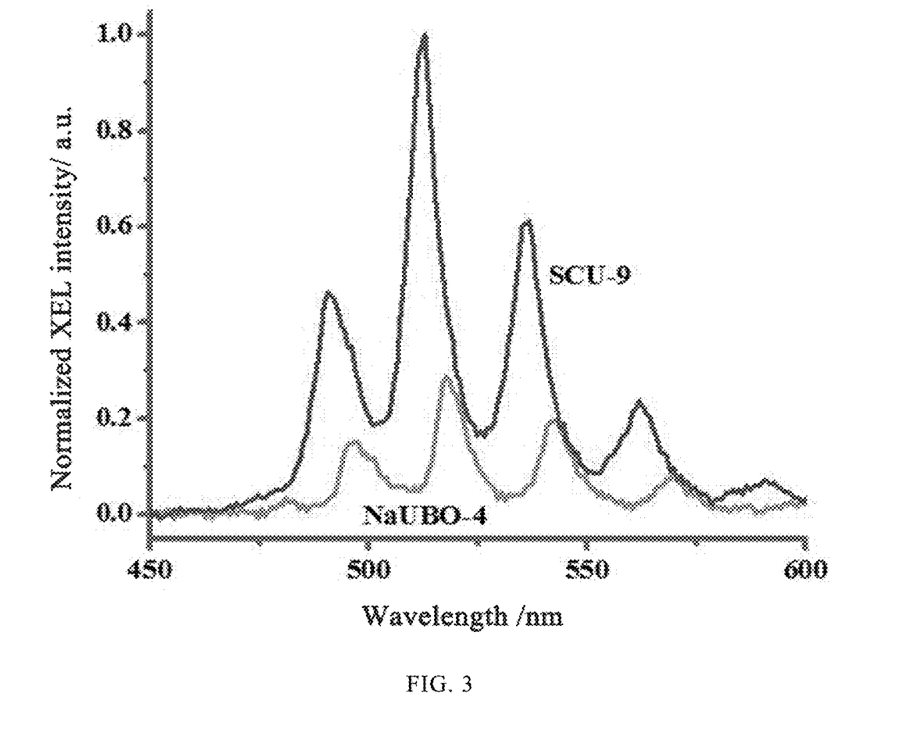
FIG. 3 shows X-ray fluorescence spectra of different materials.

An X-ray tester was used to test the X-ray fluorescence spectrum of the SCU-9 crystal. The structure of the X-ray tester is shown in FIG. 2. The sample in FIG. 2 is the SCU-9 crystal in this embodiment, and the test result is as shown by an upper curve in FIG. 3.

Figure 4:
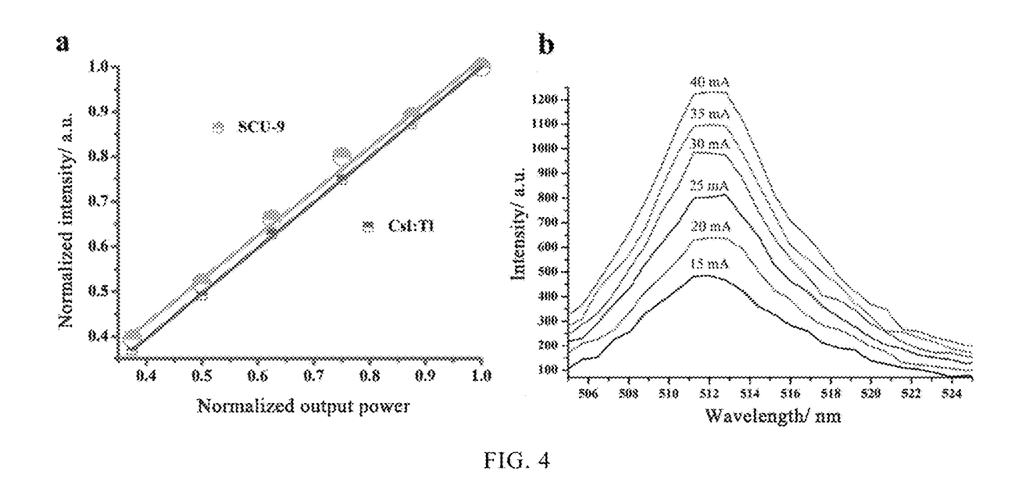
FIG. 4 shows the relationship between various X-ray powers and the fluorescence intensity of SCU-9.

In addition, the relationship between various X-ray powers and the fluorescence intensity of SCU-9 was tested. CsI:Tl was used as a control. The experimental results show that with the increase of X-ray energy, the fluorescence intensity of the sample also increases correspondingly (FIG. 4b, where the voltage is 40 kV), and the relationship between the two is linear (FIG. 4a), which is consistent with the application characteristic of scintillators.

Figure 5:
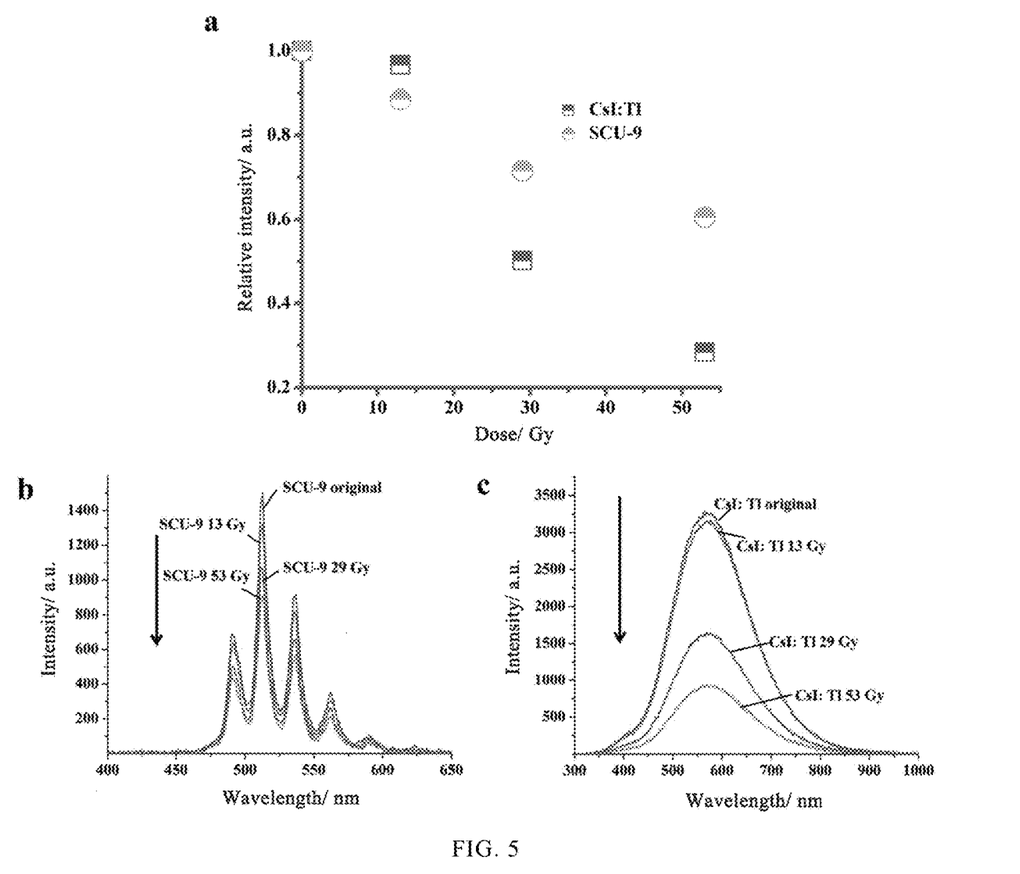
FIG. 5 shows the comparison of the irradiation stability and the variation trend in the irradiation stability of SCU-9 and CsI:Tl.
Figure 6:
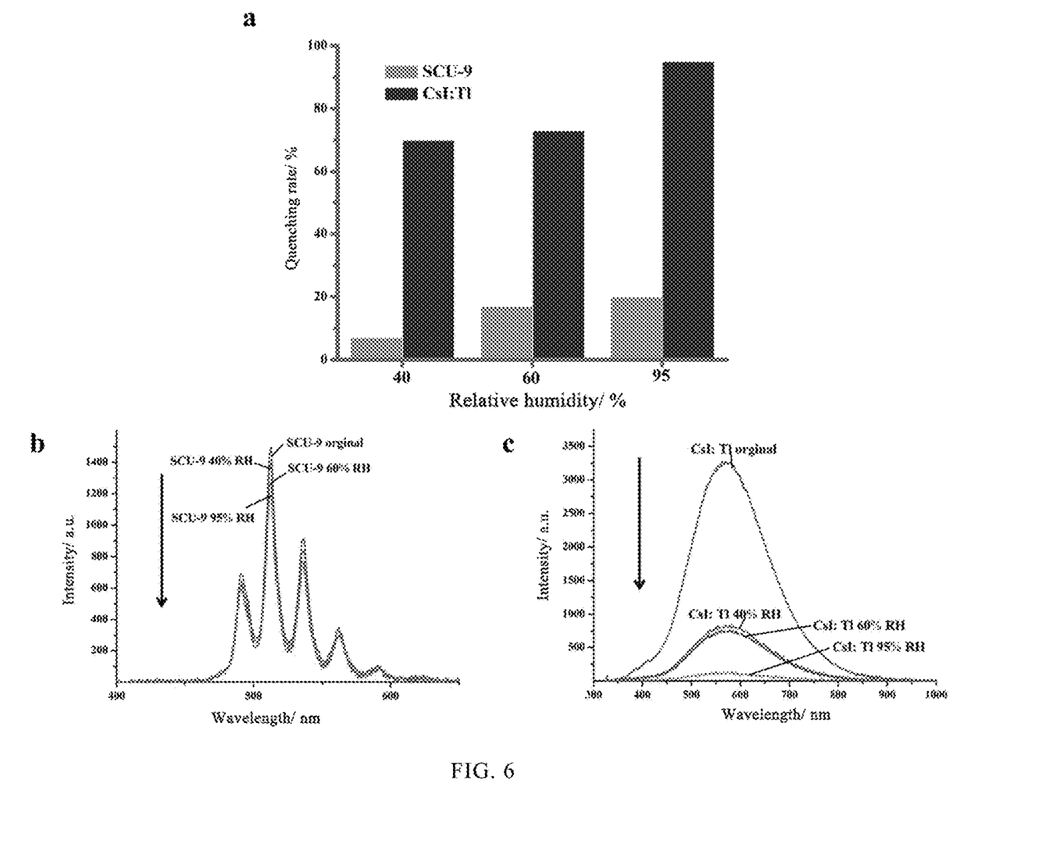
FIG. 6 shows the comparison of the humidity stability and the variation trend in the humidity stability of SCU-9 and CsI:Tl.

Luminescence stability under irradiation is another characteristic of the scintillators. FIG. 5a shows the comparison of the irradiation stability of SCU-9 and CsI:Tl, and FIGS. 5b and c show the variation trend in the irradiation stability of SCU-9 and CsI:Tl, respectively. The luminescence output of SCU-9 and CsI:Tl decreases with the increase of doses. The results show that SCU-9 still maintains a 65% luminescence output at a final dose of radiation of 53Gy. Under the same conditions, the luminescence output of CsI:Tl is only about 20%. In order to widen the scope of application, the stability of the scintillator at a high humidity is also a property needed to be determined. The experimental results are shown in FIG. 6. FIG. 6a shows the comparison of the humidity stability of SCU-9 and CsI:Tl. FIGS. 6b and c show the variation trend in the humidity stability of SCU-9 and CsI:Tl respectively. The luminescence output of SCU-9 and CsI:Tl decreases with the increase of the relative humidity. At 95% humidity, the luminescence output of CsI:Tl is decreased to 10% or less, while SCU-9 still maintains about 80% luminescence output.

Figure 7:
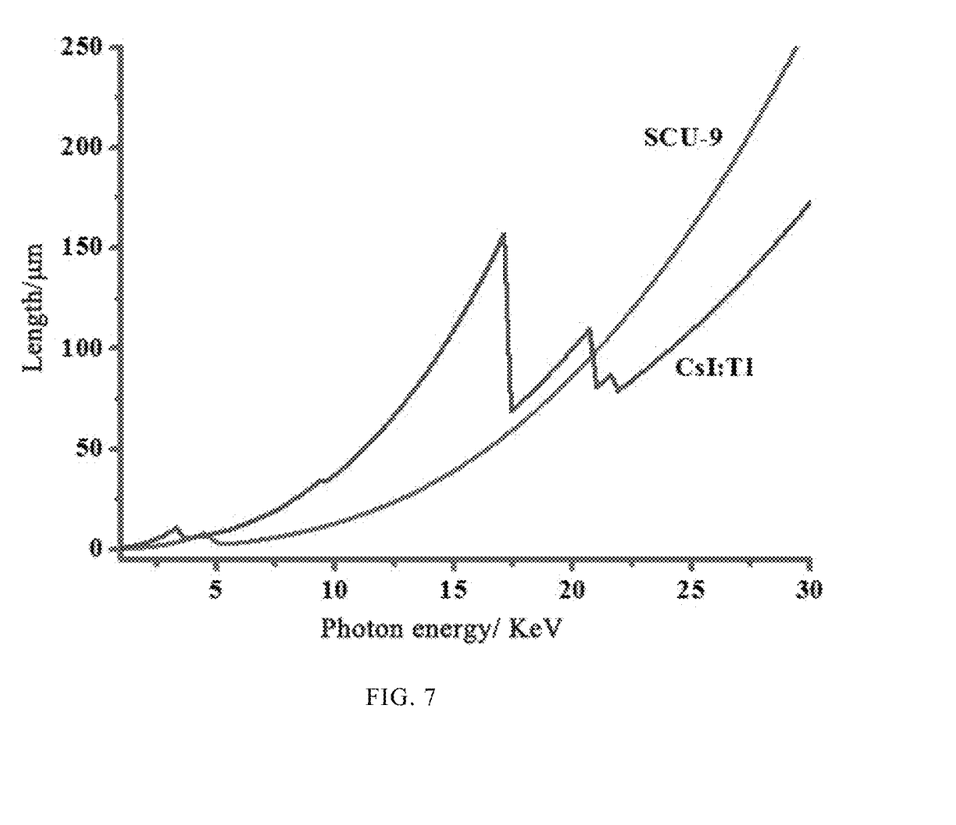
FIG. 7 shows the radiation resistance test results of SCU-9 and CsI:Tl within a range of 30 eV-30 keV X-ray energy.

The radiation resistance of SCU-9 and CsI:Tl within a range of 30 eV-30 keV X-ray energy is calculated. As shown in FIG. 7, at 20 KeV or higher, the SCU-9 compound has a stronger radiation resistance than the commercial product CsI:Tl.

Embodiment 2

Synthesis of (NaBUO-4)

NaNO₃, H₃BO₃, and UO₂(NO₃)₂·6H₂O were placed into a polytetrafluoroethylene reactor at a molar ratio of 3:15:1, a small amount of deionized water was added to dissolve the above reactants. The resulting mixture was sealed, heated up to 190° C. and heated for 1 day, and then gradually cooled to room temperature. The product was washed with a large amount of boiling water, until the boric acid was completely dissolved. The resulting crystalline product was washed with ethanol, and then air dried at room temperature, to obtain the (NaBUO-4).

Following the method as described in embodiment 1, the X-ray fluorescence spectrum of (NaBUO-4) was obtained. The result is as shown by a lower curve in FIG. 3.

Embodiment 3

An uranium-containing organophosphate of Formula (II) has a structural formula below, which is referred to as ([TMA][(UO₂)₂(1,3-pbpH)(1,3-pbpH₂)]) below:

The preparation method is as follows.

1,3-phenylenebis(phosphonic acid) (1,3-bppH₄), tetrabutylammonium hydroxide, and UO₂(NO₃)₂·6H₂O were placed into a polytetrafluoroethylene reactor at a molar ratio of 2:2:1, 1 drop of hydrofluoric acid (HF) was added, and 1 mL of deionized water was added to dissolve the reactants. The resulting mixture was sealed, heated up to 200° C. and heated for 3 days, and then gradually cooled to room temperature. The product was washed with water, and then the resulting crystalline product was washed with ethanol, and air dried at room temperature, to obtain the compound [TMA][(UO₂)₂(1,3-pbpH)(1,3-pbpH₂)], which can be used as a scintillator.

Embodiment 4

An uranium-containing metal salt of Formula (IV) has a structural formula below, hereafter referred to as Na₂UO₂(MoO₄)₂H₂O, wherein n is 1, m is 2, Y is the Mo element, and $A^{n+}$ is Na⁺:

The preparation method is as follows.

Na₂MoO₄ and UO₂(NO₃)₂·6H₂O were placed into a polytetrafluoroethylene reactor at a molar ratio of 1:4, a small amount of deionized water was added to dissolve the reactants. The resulting mixture was sealed, heated up to 200° C. and heated for 3 days, and then gradually cooled to room temperature. The product was washed with a large amount of boiling water. The resulting crystalline product was washed with ethanol, and then air dried at room temperature, to obtain the Na₂UO₂(MoO₄)₂H₂O. The compound can be used as a scintillator.

Embodiment 5

In a compound of Formula (V), X is the Cl element, and B⁺ is the structural formula is shown below, and the compound is referred to as [BTA]₂[UO₂Cl₄]:

The preparation method is as follows.

UO₂(CH₃COOH)₂·2H₂O and phenyltriethylammonium hydroxide were placed into a beaker at a molar ratio of 1:2.9, 2 mL of hydrochloric acid was added, then 10 mL of deionized water was added to dissolve the reactants. The resulting mixture was volatilized for 5-7 days at room temperature until crystallization. The product was washed with water. The resulting crystalline product was washed with ethanol, and then air dried at room temperature, to obtain the compound [BTA]₂[UO₂Cl₄]. The compound can be used as a scintillator.

The above description is only preferred embodiments of the present invention and not intended to limit the present invention, it should be noted that those of ordinary skill in the art can further make various modifications and variations without departing from the technical principles of the present invention, and these modifications and variations also should be considered to be within the scope of protection of the present invention.

What is claimed is:

1. A scintillator comprising a uranium-containing compound, wherein the uranium-containing compound is a uranium-containing organic-inorganic hybrid compound or a uranium-containing inorganic compound, wherein the uranium-containing organic-inorganic hybrid compound is a uranium-containing organic carboxylate of Formula (I) or a uranium-containing organophosphate of Formula (II):

and
the uranium-containing inorganic compound is a uranium-containing non-metallate of Formula (III), or a uranium-containing metal salt of Formula (IV):

in which m is 1 or 2, and n is for 2;
in Formula (I), $R^1$ is selected from phenyl, substituted phenyl, or alkyl;
in Formula (II), $R^2$ is selected from phenyl, substituted phenyl or alkyl;
in Formula (III), M is selected from the B, N, Si, Se, P, As, S or Te element;
in Formula (IV), Y is selected from the Mo, V, Cr, Nb, W, Re, Ga, Ge, Sb or Sn element; and
in Formulas (II), (III) and (IV), $A^{n+}$ is independently selected from tetramethylammonium cation, $Na^+$, $K^+$, $NH_4^+$, $Rb^+$, $Cs^+$, $Mg^{2+}$, $Ca^{2+}$, $Sr^{2+}$, $Ba^{2+}$, $Pb^{2+}$ or $Bi^{2+}$.

2. The scintillator as claimed in claim 1, wherein $R^1$ is phenyl or alkyl.

3. The scintillator as claimed in claim 2, wherein in Formula (I), the uranium-containing organic carboxylate is $UO_2(C_9O_6H_4)(H_2O)$, and the Formula (I) is a structural formula of:

4. The scintillator as claimed in claim 3, wherein the $UO_2(C_9O_6H_4)(H_2O)$ is prepared by steps of:
dissolving uranyl nitrate, boric acid, and 1, 3, 5-benzenetricarboxylic acid in water, sealing, and performing reaction at 190-250° C., cooling and washing the resulting solution to obtain the $UO_2(C_9O_6H_4)(H_2O)$.

5. The scintillator as claimed in claim 4, wherein a molar ratio of uranyl nitrate, boric acid, and 1, 3, 5-benzenetricarboxylic acid is 0.8-1:1-10:1-2.

6. The scintillator as claimed in claim 1, wherein in Formula (II), n is 1, $R^2$ is phenyl, and $A^{n+}$ is tetramethylammonium cation.

7. The scintillator as claimed in claim 6, wherein in Formula (II), the uranium-containing organophosphate has a structural formula of

8. The scintillator as claimed in claim 1, wherein in Formula (III), n is 1, M is the B element, and $A^{n+}$ is $Na^+$.

9. The scintillator as claimed in claim 1, wherein in Formula (IV), n is 1, m is 2, Y is the element Mo, and $A^{n+}$ is $Na^+$, $Li^+$, $K^+$, $Rb^+$ or $Cs^+$; or n is 2, m is 1, Y is the Mo element, and $A^{n+}$ is $Mg^{2+}$, $Ca^{2+}$, $Ba^{2+}$, $Pb^{2+}$ or $Bi^{2+}$.

* * * * *